(12) United States Patent
Jassan et al.

(10) Patent No.: US 7,247,377 B2
(45) Date of Patent: *Jul. 24, 2007

(54) ABSORBENT COMPOSITION OF MATTER FOR CONTROLLED RELEASE OF ESSENTIAL OILS

(76) Inventors: Genaro Casas Jassan, Bosques de Duraznos #65-305 Col. Bosques De Las Lomas, Mexico City, CP 11000 (MX); Jose Represas de Almeida, Bosques de Duraznos #65-305 Col. Bosques De Las Lomas, Mexico City, CP 11000 (MX)

( * ) Notice: Subject to any disclaimer, the term of this patent is extended or adjusted under 35 U.S.C. 154(b) by 0 days.

This patent is subject to a terminal disclaimer.

(21) Appl. No.: 11/250,306

(22) Filed: Oct. 14, 2005

(65) Prior Publication Data

US 2006/0078733 A1 Apr. 13, 2006

Related U.S. Application Data

(63) Continuation-in-part of application No. 10/642,920, filed on Aug. 18, 2003, now Pat. No. 7,163,737, which is a continuation-in-part of application No. 09/856,196, filed on Sep. 4, 2001, now Pat. No. 6,635,344.

(51) Int. Cl.
  *B32B 5/16* (2006.01)
  *A61L 9/04* (2006.01)
  *A61L 9/013* (2006.01)
  *B01J 20/24* (2006.01)

(52) U.S. Cl. .................. 428/403; 119/171; 119/172; 241/24.2; 428/407

(58) Field of Classification Search ................ 428/323, 428/326, 327; 119/171, 172; 241/24.1, 241/24.2

See application file for complete search history.

(56) References Cited

U.S. PATENT DOCUMENTS

| | | |
|---|---|---|
| 3,617,564 A | 11/1971 | Vander Hooven et al. |
| 3,921,581 A | 11/1975 | Brewer |
| 4,053,112 A | 10/1977 | Vander Hooven et al. |
| 4,296,709 A | 10/1981 | Schulein, Jr. |
| 4,519,340 A | 5/1985 | Dickey |
| 5,062,954 A | 11/1991 | Leedy et al. |
| 5,064,407 A | 11/1991 | Peiffer |
| 5,152,251 A | 10/1992 | Aukeman et al. |
| 5,160,629 A | 11/1992 | Brown |
| 5,207,387 A | 5/1993 | Bergstrom |
| 5,207,389 A | 5/1993 | Hall et al. |
| 5,878,696 A | 3/1999 | Gerling et al. |
| 5,891,937 A | 4/1999 | Berg et al. |
| 6,053,125 A | 4/2000 | Kory et al. |
| 6,635,344 B1 | 10/2003 | de Almeida et al. |
| 6,936,344 B2 | 8/2005 | Represas de Almeida et al. |
| 6,994,752 B2 | 2/2006 | Estrada et al. |
| 7,163,737 B2 * | 1/2007 | De Almeida et al. ....... 428/323 |

FOREIGN PATENT DOCUMENTS

| | | |
|---|---|---|
| EP | 0470596 | 2/1992 |
| ES | 419420 | 4/1976 |
| FR | 2598280 | 11/1987 |
| WO | WO-9854956 | 12/1998 |

* cited by examiner

Primary Examiner—H. Thi Le

(57) ABSTRACT

An absorbent composition of matter acts as a carrier for an active ingredient. The active ingredient is gradually released by the carrier in a controlled manner, which is compatible with the environment and current tendencies towards the use of organic and biodegradable products. The carrier is characterized as being particles obtained from the milling, separation, air wash and classification of the different fractions obtained from corncobs. The active ingredient is, for example, an essential oil, such as garlic oil or extract that may be combined with other essential oils for a synergistic effect that results in an improved insecticide/fungicide that is natural and contains no chemical additives. Alternatively, an artificially obtained substitute, for example, allyl isothiocyanate (AITC), can be used as a substitute for mustard seed oil.

15 Claims, 2 Drawing Sheets

ABSORBENT COMPOSITION OF MATTER FOR CONTROLLED RELEASE OF ESSENTIAL OILS

CROSS-NOTING TO RELATED APPLICATIONS

This application is a Continuation-In-Part application of application Ser. No. 10/642,920, filed on Aug. 18, 2003 now U.S. Pat. No. 7,163,737, which is a Continuation-In-Part application of application Ser. No. 09/856,196, filed on Sep. 4, 2001 now U.S. Pat. No. 6,635,344, which claims the benefit of PCT Application No. PCT/MX00/00034, filed Sep. 13, 2000, which claims the benefit of Mexican Application No. 998523, filed Sep. 17, 1999, the entire contents of which are herein incorporated by reference.

BACKGROUND OF THE INVENTION

1. Field of the Invention

The present invention relates to an absorbent composition of matter used to gradually release an active ingredient, such as a natural pesticide made from essential oils, for inhibiting the growth of bacteria, fungi and eradicating insect pests.

2. Description of the Related Art

Commercially available insecticides, including those available for home use, commonly comprise active ingredients or "poisons" which are not only toxic to the target insect pests, but, if used in relatively confined environments and delivered as aerosol sprays, can be present in sufficient concentration to also be toxic to humans and household pets. Various undesirable side effects may include immediate or delayed neurotoxic reactions, and/or suffocation. Even the noxious odor of such materials can cause headaches or upset stomachs in some individuals. These adverse side effects are exacerbated when such compositions come in contact with persons of increased sensitivity, or persons of small body mass such as children or babies.

For some time, efforts have been made to develop insecticidal compositions, particularly those intended for residential use in aerosol form, which are effective in killing the targeted insect pests completely and quickly, but non-toxic to humans and pets. The Environmental Protection Agency (EPA) regulates the use of potentially toxic ingredients in pesticidal compositions under the Federal Insecticide, Fungicide and Rodenticide Act. Certain materials considered to be either active or inert materials by the EPA have been deregulated or otherwise identified as acceptable "safe" substances offering minimum risk in normal use. Other materials are currently undergoing investigation and may be deregulated in due course. Deregulated substances are generally considered non-poisonous by the consumer. Thus, the term "non-poisonous" as used herein is intended to convey a composition that, while highly effective in killing targeted insect pests, is safe to use around humans, particularly small children, and pets.

Unfortunately, non-poisonous insecticidal compositions available heretofore incorporating deregulated materials as the active ingredient have had limited efficacy. Attempts to use deregulated essential oils as the active ingredient in such insecticides, while having limited success, have generally been found to be either cost prohibitive, inadequately lethal to control a range of targeted insect pest species, or too slow-acting to enable the user to confirm that the insect has been killed and to dispose of the dead insect so as to avoid polluting the environment.

Many commercial products contain components which exercise a beneficial effect for only a limited time after introduction into their intended environment, being rapidly consumed, metabolized, vaporized or otherwise lost. To have continued effectiveness, such products must be reapplied at intervals, providing an undesirable and perhaps harmful excess at the times of reapplication and barely adequate levels at later times.

Microencapsulation techniques address the problem of controlled release by enclosing the transient component within hollow shells of differing size and wall thickness, which dissolve or otherwise rupture at different intervals to provide a more or less steady supply.

The temporary shells of microencapsulation can be replaced by more permanent semipermeable shells which allow escape through the shell wall without shell destruction, or the entire microcapsule replaced by a homogeneous semipermeable vehicle containing the active ingredient as a pure impregnant, solute or precipitate. In this latter process, the host vehicle serves not to enclose the active ingredient within a wall, but as a carrier from which it can only slowly escape by solution, diffusion, evaporation or some other rate-limited process. The utility of a particular host material as such a carrier depends on such properties as liquid content, pore size, compatibility with various environments, surface energy and wettability, susceptibility to post-impregnation modifications in properties, and ease of manufacture in suitable physical forms. The commercial exploitation of slow release carrier vehicles requires the availability of inert, microporous materials which are readily impregnable with a wide variety of substances, have controllable porosity, and possess acceptable physical properties.

Garlic (*Allium sativum* Linn.) and/or its extract have been reported to have antibacterial and/or antifungal properties. It is known that Allicin isolated from the cloves of garlic had antibacterial properties against both Gram positive and Gram negative bacteria. Further, aqueous extracts of garlic have been reported to inhibit the growth of a variety of yeast-like fungi in the genera *Candida, Cryptococcus, Rhudotoruto, Torulopsis* and *Trichosporon*. It has also been previously reported that garlic extract and chips inhibit the growth of fungi such as *Candida albicans, Aspergillus fumigatus* and *Aspergillus parasiticus*. Because of its antifungal and antibacterial properties, garlic or its extract have been used as pesticides to control plant diseases such as mildew. It has also been used as an insecticide to control plant insects such as army worms, aphids and Colorado beetles. Most recently, garlic extract and water has been used to repel mosquitoes.

Therefore, there is a need in art for a safe, cost effective and highly efficient absorbent composition of matter that provides for a controlled time release of an aromatic substance, such as an essential oil or a combination of essential oils. One use of essential oils is to repel plagues of insects in the home as well as other agricultural crop damaging inserts.

SUMMARY OF THE INVENTION

The concept of the new product derived from the present invention, is enlarged in its range of applications. For example, uses in agriculture, home and industry are possible by combining its qualities to gradually release an aromatic substance to repel plagues of insects like cockroaches in kitchens or mosquitoes as well as other agricultural crop damaging insects. Good results are obtained by combining garlic or garlic extract, known for its qualities as a repellent for garden or agriculture damaging insects, and essential oils, such as eugenol, with this absorbent carrier.

Additionally, the absorbent carrier has the capacity to gradually release these forms of repellent aromas providing for a long lasting product; malodor, if present is also totally or partially absorbed. Inversely, attractant substances can be used, being of particularly useful application for household pets, for example, the use of an attractant aroma or fragrance in the production of cat litter. Additionally, the composition of matter in the present invention provides for a controlled time release of the different active ingredients, such as a natural pesticide, applied to the preferred embodiment (corn cob particles).

Essential Oil is defined as a subtle, volatile liquid obtained from plants and seeds or artificially obtained substitutes, for example, allyl isothiocyanate (AITC) as a substitute for mustard seed oil. Garlic or garlic extract is defined as any liquid removed from cloves of garlic and may therefore include garlic oil and water. Garlic extract has the same meaning as garlic juice.

In one aspect of the invention, an absorbent material comprises a carrier formed by particles obtained from one of a woody ring and a chaff ring of a corncob; and an active ingredient mixed with said carrier, wherein said active ingredient comprises an essential oil.

DESCRIPTION OF THE PREFERRED EMBODIMENT

Figure 1:
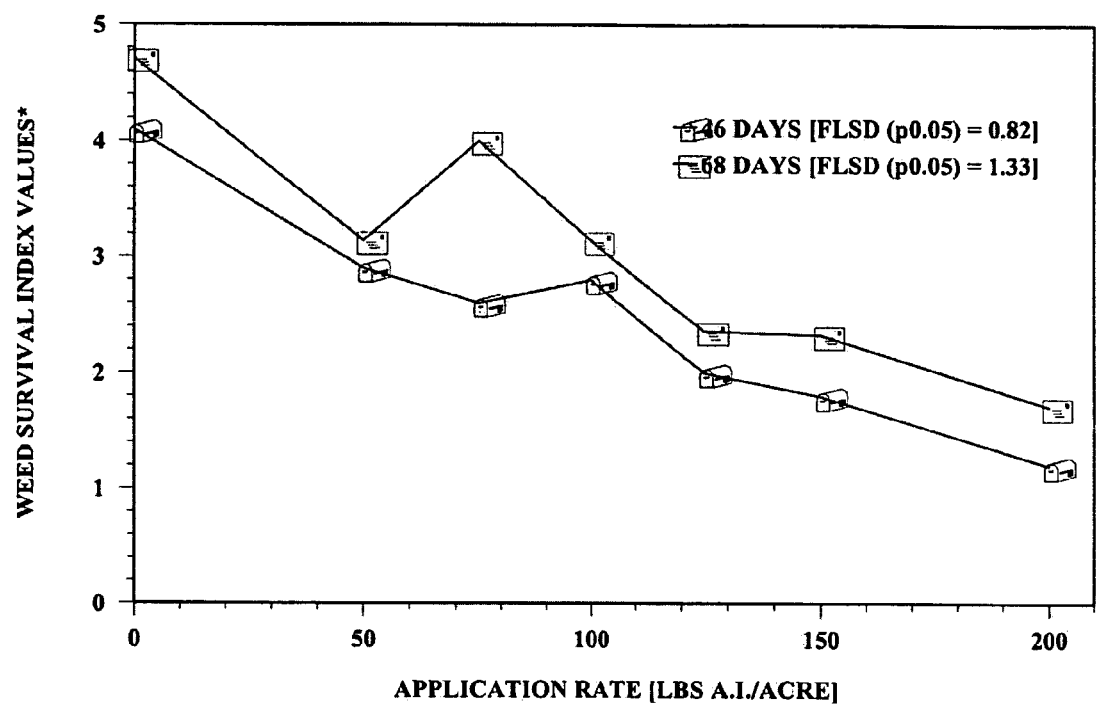
FIG. 1 shows the relationship between weed survival and application rate of a slow release formulation containing 85% garlic and 15% mustard oils in a microplot experiment with *Impatiens*.

The preferred embodiment of the product object of the present invention consists of two basic elements: first, a carrier characterized by its great capacity for odor and malodor absorption, and gradual release of other active substances toward the air or surrounding atmosphere. Second, one or more chemical, natural or synthetic elements that added to the carrier complete diverse functions, according to the desired results (perfume surrounding air, react with undesirable substances present in the air, liberate therapeutic, repellent or attractant chemical agents).

The carrier which is the preferred embodiment of the product in the present invention is a material obtained from the threshed ear of corn (*Zea Maiz*) whose special physical and chemical qualities allow the previously described functions, of absorption and gradual release. To obtain the different components that comprise the threshed ear of corn, an industrial process, well known in the state of the art is required, which consists of separation, classification and sizing of each one of the components that constitute corncobs.

The threshed ear of the corn, also known as "olote" in Mexico, "spiga de maiz" in Castilian, corncob in English, "sabugo" in Portuguese and "balle de maïs" in French, if cut transversely is constituted by three concentric ring. Starting with the inner ring, they are known in English as pith, woody ring and chaff. The material of the present invention uses the woody ring and chaff portions.

The woody ring, as well as the chaff portion, has similar characteristics, both can be used as carriers for active ingredients as described in the body of the present invention. The main differences reside in the difference of absorption capacity and in the particle hardness. Other differences exist and are described below.

In order for the woody ring to comply with the requirements of the present invention it must have the following characteristics: woody ring should be 99% free of other cob particles, it should have no more than 1% dust or fines (the product should be air washed). By definition, fines are particles that can pass through U.S. standard screen size 400 (37 microns). It must be subjected to heat treatment that guarantees microbiology content and moisture levels under 10%. For correct functionality, the particle size should be uniform in size and ranges should not exceed a maximum of 3987 microns and a minimum of 42 microns.

The woody ring of corncobs is characterized by the following: a hardness of 4.5 on the Mohs scale, a fast absorbency of oil (for example soybean oil) of 1 to 1 on weight basis and the typical molecular structure of a natural fiber. Ideally particle sizing for the present invention should be between the following ranges: 1) retained or larger than a mesh of 3987 microns, 2) particles between 3987 and 1191 microns, 3) particles between 1191 and 841 microns, 4) particles between 841 and 42 microns.

The main characteristic of the particle size is the surface area that each one represents; for example, particles between 1410 and 841 microns have an average surface area of 5.88 square meters per gram. Particles between 841 and 420 microns have an average surface area of 7.20 square meters per gram. This characteristic is decisive in the qualities of absorption of different substances on the part of the carrier that embodies the product object of the present invention.

It is necessary to highlight that woody ring particles are characterized by having a structure that seen on an electron microscope resembles that of a sea sponge. One can infer that this type structure has capacity to admit and retain substances of small and large molecular size. This allows superior qualities of absorption in comparison to other products such as Cyclodextrin that as is known in the state of the art, only admits malodor molecules of small size.

The separate and classified sizes of woody ring have unique qualities for the absorption of scents from the air in contact with them. To illustrate this, diverse laboratory tests were made with surprising results as follows:

Example #1: A 100 gram portion of mature Camembert cheese, a 20 gram portion of bacon and a 10 cm dish containing 25 grams of woody ring particles sized between 1410 and 841 microns where all placed in a sealed glass container. Another glass container with the same components except for the woody ring particles was also prepared as a control sample. Both glass containers were inspected at intervals of 24 hs, 3 days, 5 days and 8 days; the container with the absorbent material practically didn't manifest the characteristic scent of the decomposition of products contained, while the control glass container presented potent and unpleasant scents.

Example #2: 10 grams of tobacco where incinerated in two sealed glass containers. One of the containers had a 10 cm diameter dish containing 10 grams of woody ring, sized between 1410 and 841 microns. The other container remained as a control sample. After 24 hours both containers where opened. The container with the absorbent woody ring particles did not present the characteristic scent of tobacco, while the control sample presented potent scents characteristic of tobacco smoke.

In both tests the evaluation of the scents or aromas were carried out by the authors of the present invention, as well as by a professional perfumist whose educated sense of the smell surrendered an objective opinion of these tests.

The characteristics of the Chaff portion of the corncob are similar to the woody ring portion in its ability to function as a carrier for fragrances and other active ingredients. The most distinguishing differences are: 1) more absorption; between 1.5 and 3 times it's weight in oil, 2) Particles size between 841 and 73 microns and 3) less particle flowability. Woody ring particles are rounder in shape than chaff and therefore flow better.

This physical difference between woody ring particles and chaff particles is translated into functional differences in the ability to absorb undesirable scents from the air. Additionally the granular form of the woody ring allows for more interparticle space for air-flow. While the smaller closer chaff particles allow less airflow.

Both woody ring and chaff are characterized by having an almost neutral pH, in the order of 6. This quality makes it an ideal inert carrier with all type of substances, since it does not react with active ingredients. Some other types of carriers have to be disactivated first to neutralize their pH content.

The physical and chemical characteristics of corncobs are not favorable for the development of microorganisms, therefore not providing fertile ground for bacteria or fungi that in turn cause malodor or disagreeable scents. It is known in the state of the art that a whole corncob can be stored without cover for periods of one year.

The functional differences of the woody ring portion (flowability and larger interparticle space) and that of the chaff (more absorption) allow for a great diversity of applications and use. These corncob fractions can be used combined or separately, for different applications, that are described for the absorbent carrier that integrates the product object of the present invention.

For example, if the functional objective, is the absorption of an active substance to be slowly released in the air and at the same time allowing the flow of malodor air to be absorbed, the suitable product is the one obtained from the woody ring. If on the contrary the functional object is to achieve absorption of an active substance to be slowly released in the air and the absorption of malodors or scents is not important, the elected product would be the chaff portion.

Other approaches to select the corncob fraction can be: the convenience of not having powders or fines. An example of such an application is the integration of the absorbent agent to active filtration systems where the use of the product from the woody ring is most suitable. If the active ingredient required is thick in nature or if product were required to be molded in a three-dimensional object (including the making of pellets), one would be inclined to select the chaff portion.

On the other hand, and a substantial element of the composition of matter, object of the present invention, are the active substances or ingredients to be used. These can be aromas, perfumes, flavors or other natural or chemical agents that are integrated to the product derived from the composition of matter object of the present invention. In general these substances are available in a liquid, powder or granular state and depending on the active agents chemical constitution, soluble in oil or water.

Under these conditions the absorbent carrier, depending on the type of active ingredients used, can absorb a larger or smaller quantity of said agent. This depends primarily on the size of the active ingredient molecule size, the absorbent carriers gradual release will also depend on this molecular size. The absorption of malodor or scents is simultaneously achieved. The intensity, duration and brightness of the aroma, with fragrances, will depend on factors of the active ingredient or agent's composition. For example, larger molecular size is equal to longer duration, while the presence of smaller molecular sizes such as those in an ester evaporate quickly.

Some examples for the formulation of the absorbent carrier with active substances in a liquid state are:

EXAMPLE #1 for fragrances, perfumes and therapeutic aromas, generally using a base of polyvinyl glycol, light mineral oil or microencapsulated powder or granular base, the concentration on a weight basis of the woody ring to active ingredient, is from 0.01% to 18%. A larger amount saturates the absorbent carrier and product flowability is greatly reduced. The concentration on a weight basis of the chaff portion to active ingredient is from 0.01% to 36%.

EXAMPLE #2 for repellents and attractants, generally in oleaginous or microencapsulated powder or granular bases such as Givaudans Flavor Burst™ products, the recommended concentration ranges, for the woody ring as well as the chaff portion, are similar to the previous example. Concentrations depend on the active ingredient or agent used and the functionality desired in the end product.

EXAMPLE #3 for oxidizers and chemical reducers or neutralizers, generally in a liquid or solid microencapsulated powder or granular base, the concentration ranges on a per weight basis, both for woody ring and chaff are from 0.05% to 5% of active ingredient or substance. Being that the determinant factor is not the capacity of carrier absorption, but rather the capacity to stay stable and not be affected by the active substance.

EXAMPLE #4 for antibacterial and fungicidal use, when these are in a water, oleaginous or microencapsulated powder or granular base, the proportion of active ingredient or agent on a per weight basis to absorbent carrier is the same as that of example #1. When the active ingredient uses a water base, the concentrations on a per weight basis can range from 0.01% to 25% with the woody ring fraction and 0.01% to 50% with chaff. The concentration to choose will be determined by the experience of whom ever prepares formulations according to the known state of the art.

Additionally as mentioned in previous examples, the formulation of the composition of matter or product object of the invention, can be made using liquid based active ingredients added to the absorbent carrier. The possibility also exists for the use of solid materials as active ingredients, usually in the form of pure or microencapsulated products. This variation allows more flexibility in the absorbent carriers applications. It can also take advantage of factors like stronger concentrations of active ingredients. Many pure substances come in solid form; the use of a liquid as diluent or dispersant of the pure substance implies a reduction in its concentration or strength. For example table salt NaCl is more intense to the palate than its version diluted in water, commonly called brine.

On the other hand the use of active ingredients in solid state can adhere and/or adsorb to the surface of the absorbent corn cob carrier, allowing it to use a larger proportion of it's inner absorbent capacity for malodor or other applications. The opposite occurs when using active ingredients in a liquid state, since these occupy more of the corncob carriers odor absorbent capacity thus partially reducing it's ability to absorb undesirable malodor.

The option of using active ingredients in solid state instead of liquid, is possible with the concurrence of 4 basic elements: an absorbent carrier, constituted by a fraction derived from corncobs, an active ingredient or agent that is in liquid or solid state; a combination resulting from the mix of a mineral or organic carrier with a liquid base active ingredient and finally, a substance that assures that, the active ingredients absorb or adsorb to the corncob carrier (avoiding the separation among carriers or agents and assuring correct homogeneity, functionality and dispersion).

To exemplify the above-mentioned we describe two practical examples. The results obtained, using two types of active ingredients one in liquid form and the other solid, both dispersed in the corncob carrier; woody ring sized between 1410 and 841 microns was used. The liquid active ingredient is a concentrated floral fragrance perfume using polyvinyl glycol as a carrier.

EXAMPLE #5

Corncob carrier mixed with an active ingredient in a liquid base. The density of the active ingredient determined a saturation point of 18% on a per weight basis to the corncob granules. 180 grams of active ingredient where mixed with a kilogram of corncob carrier. This proportion maintains carrier flowability, absorption of odors and slow release of active ingredient (fragrance).

Results: the perfuming active ingredient, was released gradually and perceived smell lasted 30 days. The corncob carrier continued absorbing scents in the air after 30 days.

EXAMPLE #6 two active ingredients; one utilizing an encapsulated active ingredient, commercially available, like Givaudan fragrance or flavor, in powder form and the other, using a laboratory sample, made by mixing Silicon Dioxide ($SiO_2$), in proportion of 1 to 4 on the base of liquid active ingredient to Silicon Dioxide weight. The absorbent corncob carrier was impregnated with an adherent coating, in this case consisting of a 0.5% per weight basis, foamed solution of anionic surfactant with water. Once the corncob carrier was mixed with the foam, an adherent coating of foam formed on the corncob granules. Immediately after which the active ingredients in solid form where added. The active ingredient particles adhered to the coating and allowed for a homogeneous mixture without separation.

Results: In both cases the adhesion of solid particles to the corncob granules allowed a more intense and prolonged duration of the perfuming scent, which was slowly released over a 60 day period, in comparison to the 30 days obtained in example #5 with a liquid active ingredient perfume mixed directly with corncob granules. In both cases the corncob absorbed odors in the air even after 60 days.

Both examples, one with liquid and the other with solid active ingredients were performed at the same time. The new product was exposed to the air by placing it in a 40 cm by 5 cm dish. The product was placed in two separate rooms measuring 3×4×2.4 mts.

The adherents used to form a coating on corncob particles are within the following ranges:

EXAMPLE #7

Using surfactants as adherent coating: anionic, cationic and amphoteric can be used. The formulation is: foam obtained from adding water to 0.02% to 5% of surfactant by weight. The quantity of foam on a per weight basis to corncob woody ring fraction (carrier) is between 0.5% and 3.5%. Larger proportions do not allow for an appropriate mixture when adding active ingredients in solid form.

EXAMPLE #8

Using mineral oils as an adherent coating; they should be highly refined preferably odor and colorless; viscosity on the Saybolt scale (SUS/210 F) should be between 40 and 300. The concentration of mineral oil by weight to woody ring is between 0.5% and 18%.

EXAMPLE #9 for natural pesticides, generally using a base of essential oil or microencapsulated powder or granular base, the concentration on a weight basis of the woody ring to active ingredient, is from 0.01% to 18%. A larger amount saturates the absorbent carrier and product flowability is greatly reduced. The concentration on a weight basis of the chaff portion to active ingredient is from 0.01% to 36%.

Tests were conducted to determine the effectiveness of the absorbent composition used as a carrier for the active ingredient comprising an essential oil of the extract of garlic and/or allyl isothiocyanate (AITC) for the controlled release of the garlic extract against golden nematode in alpha potato. The treatment consisted of the application of 7 kg/hectare, 10 kg/hectare and 15 kg/hectare of the carrier and essential oil. The results indicate that the golden nematodes were greatly reduced as compared to a control, while productivity was greatly increased.

In another test, the effectiveness of the absorbent composition was used as a carrier for the essential oil of garlic and/or AITC for the controlled release of the garlic against *Meloidogyne Incognita* nematode. *M. Incognita* soil was obtained from a farm in Mexico. The farmer had previously reported nematode infestation. The farmer mostly exports Tomato and other agricultural product to other countries. The carrier and garlic in the form of powder garlic was suspended in water at a concentration of 10.0 ml/l. The results indicated that the amount of larva of *Meloidogyne Incongmita* in 200 cc of soil was virtually eliminated. Further tests conducted in laboratories and greenhouses indicate similar results.

EXAMPLE #10 for nematicide/soil fumigants, generally in oleaginous or microencapsulated powder or granular bases, such as Givaudans ENROBED™ and FLAVORBURST™ products, the recommended concentration ranges, for the woody ring as well as the chaff portion, are similar to the previous example. Concentrations depend on the active ingredient or agent used and the functionality desired in the end product.

Experiment #1

The pesticidal activities of proprietary slow-release formulations of selected volatile compounds of plant origin were studied in greenhouse and microplot experiments. The selected volatile compounds were: natural thyme (20% oil) flavor; natural rosemary (20% oil) flavor; natural eugenol (20% oil) flavor; natural garlic (10% eugenol (20%); natural garlic (8.75%) eugenol (26.25%); artificial cinnamic aldehyde (20% oil) flavor; natural and artificial garlic (10%) cinnamic aldehyde (5%) flavor; natural and artificial garlic (10%) cinnamic aldehyde (10%) flavor; natural garlic (15% oil) flavor; natural and artificial garlic (12.75%) mustard (2.25%) flavor; natural and artificial garlic (85%) mustard seed (15% oil) flavor; and natural and artificial garlic (17%) mustard seed (3% oil). The compounds were encapsulated in micro-granules to form slow-release formulations. All these materials are used commonly in the food and perfume industries and are available from Givaudan of Switzerland.

In a greenhouse nematode experiment, the formulations were applied as a suspension (400 mgs granules/100 ml water) onto the soil surface of pots (10-cm diam, PVC) containing each 1 kg soil. The soil was a silt loam (pH 6.2; CEC <10 meq/100 g soil; org. matter <1.0%) from a cotton field infested with root-knot (*Meloidogyne incognita*), spiral (*Helicotylenchus dihystera*), and lesion (*Pratylenchus brachyurus*) nematodes as the main phytopathogenic species. Immediately after treatment each pot was covered with a clear 1.5 mil thick low density polyethylene bag held tight against the outer wall of the pot by a rubber band. Each treatment and control was represented by 7 replications (pots) arranged in a randomized complete block design on a greenhouse bench. Eight days after application, the bags were removed and soil samples (100 $cm^3$) were collected from each pot for nematological analysis (salad bowl incubation) and the pots were then planted with 'Hutcheson' soybean (5 seed/pot). After seven weeks the plants were removed from the pots, data on plant growth were recorded and final soil samples and roots were incubated to determine nematode numbers.

Soil and root populations of the root-knot nematode were significantly reduced by applications of thyme, rosemary and eugenol alone, and in combinations with garlic. Also, some combinations of garlic with mustard, notably the 85-15 ratio of garlic to mustard, were very active against the nematode while formulations with cinnamic aldehyde alone or with garlic were generally ineffective. Numbers of spiral nematodes in the roots were lowest in plants from pots treated with garlic-mustard combinations or with thyme. Rosemary treatments increased root populations of the lesion nematode while the other treatments had no effect on this nematode. Treatments without mustard resulted in the tallest plants with the heaviest roots and shoots. The inclusion of mustard in the formulations resulted in either no change in shoot height or in smaller increases in shoot and root weights when compared to the other formulations.

Experiment #2

The fungicidal action of the slow-release formulations used in Experiment #1 was assessed in an experiment with a sand-peat mix infested with a virulent isolate of *Rhizoctonia solani* obtained from diseased cotton seedlings. Application of slow release granules was by mixing directly with the sand-peat mix contained in pots (1 kg mix). The pots were covered with polyethylene bags and placed in a cool (20 C) room for 4 days when the bags were removed and 30 annual morningglory (*Ipomoea* spp.) seed were spread on the sand-peat surface and then covered with a 1 cm thick layer of moist sand. The pots were placed back in the cool room for two days and were then transferred to a greenhouse bench. Statistical design was as described for the experiment with nematodes. The number of morningglory plants was determined at 10, 12, 14, and 17 days after application of the formulations. Following the last count the plants were separated from the sand-peat medium, and were washed and weighed. The condition of the root systems was assessed visually using a scale of 1-5 where 1 represented perfectly healthy roots and 5 roots with restricted root system with severe necrosis and lesions caused by the fungus. Efficacy was based on calculation of the area under the curve defining the number of morningglory plants per pot (Y axis) and days after treatment for the period between the 10 and 12 days after application (X axis).

*R. solani* eliminated over 70% of the possible morningglory plants. The disease was most successfully dealt with by formulations containing garlic oil. Least active compositions were those containing cinnamic aldehyde, rosemary, and thyme in increasing order of efficacy. Granules with eugenol were the most effective among the single component formulations. The most effective compound formulations were those containing garlic+eugenol 8.75-26.26% and garlic+mustard 12.75-2.25%; these formulations were the only ones with increased fungicidal activity over that obtained with garlic alone.

Figure 2:
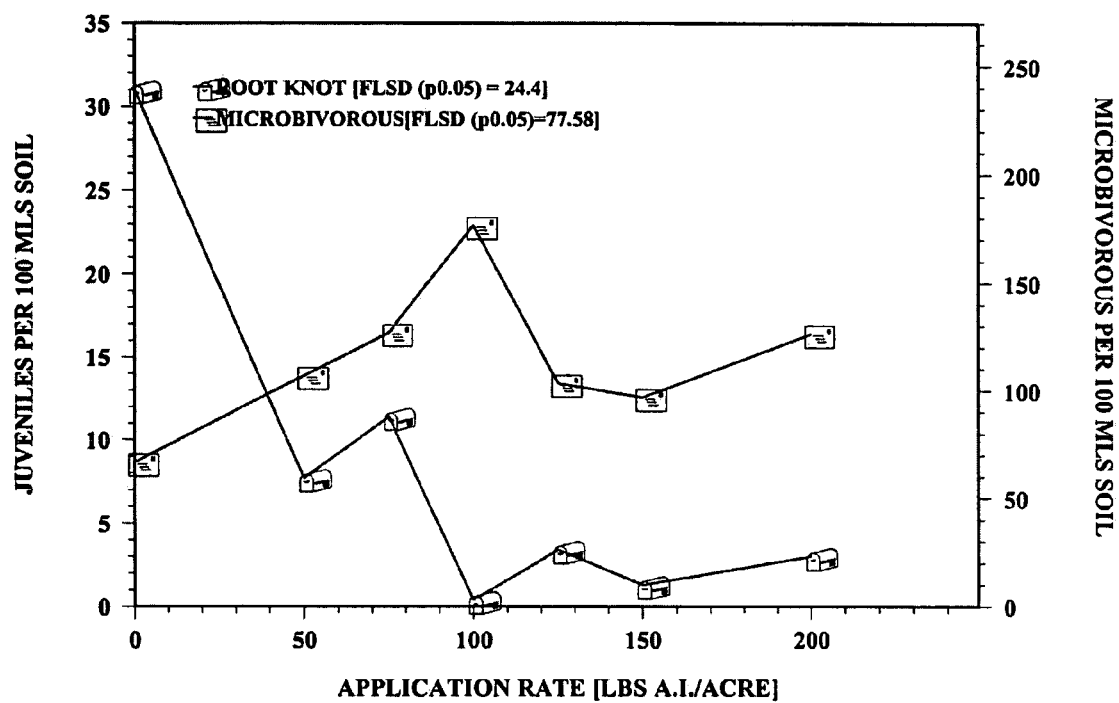
FIG. 2 shows the relationship between nematode numbers and application rate of a slow-release formulation containing 85% garlic oil and 15% mustard oil in a microplot experiment with *Impatiens*.

The herbicidal and nematicidal activities of a slow release formulation containing 15% mustard oil and 85% garlic oil was tested in a microplot (1 $ft^2$) experiment with soil infested with root-knot nematode (*M. incognita*) and a variety of annual weeds. The formulation was applied by drenching (1" acre water) at rates 0-200 lbs a.i./A, followed by coverage of the plots with clear polyethylene (1 mil). After 10 days the plots were planted with 4-week old *Impatiens* seedlings. Weed control was directly proportional to the amount of active ingredient applied, as shown in FIG. 1. Final populations of microbivorous nematodes were not affected by the treatments; however, root-knot juveniles were controlled or eliminated by rates $\geq$100 lbs ai/A, as shown in FIG. 2. Decline in numbers of root-knot nematode juveniles in relation to rates was adequately described by exponential functions. Final populations of microbivorous nematodes were not affected by the treatments.

Data from the study suggested encapsulation may be useful for development of formulations with herbicidal, fungicidal and nematicidal activities based on natural compounds with high vapor pressures. In addition, a combination of garlic extract and essential oil has a synergistic effect that significantly increases the effectiveness of garlic and/or garlic extract alone. The ideal ratio of garlic to essential oil is 85% garlic to 15% essential oil, such as eugenol, mustard seed, or the like.

Finally active ingredients can be polymers, perfumes, oxidizers, attractants, repellents, reducers, antibacterials, etc, in solid form. These ingredients are mixed and dispersed with the granular corncob carrier sized between 42 and 3987 microns. The quantity of solid active ingredient dispersed should be between 0.01% and 40% per weight basis.

In conclusion, the incorporation of corncob fractions mentioned with active ingredients whether chemically synthesized or natural, improves the qualities and functionality that both elements have for themselves separately. However, the use of corncob fractions as absorbent of odoriferous substances from the environment is also a novel concept. The forms of carrying out the mixture or integration of these elements can vary according to the circumstance. The types of active ingredients that will be used depend on the functional objective that is pursued, equipment available and the experience of those skilled in the art.

While the invention has been specifically described in connection with certain specific embodiments thereof, it is to be understood that this is by way of illustration and not of limitation, and the scope of the appended claims should be construed as broadly as the prior art will permit.

What is claimed is:

1. An absorbent composition of matter for controlled release of essential oils, comprising:
   a carrier consisting of particles obtained from woody ring and a chaff ring of a corncob; and
   an active ingredient mixed with said carrier,
   wherein said active ingredient comprises an essential oil.

2. The composition of claim 1, wherein said essential oil is selected from the group consisting of garlic, rosemary, thyme, eugenol, mustard seed oil, or any combination thereof.

3. The composition of claim 1, wherein said carrier has a content of less than 1% of fines by weight and a moisture content below 10%.

4. The composition of claim 1, wherein the particles of said carrier have a size ranging between 73 and 841 microns.

5. The composition of claim 1, wherein said essential oil comprises allyl isothiocyanate (AITC).

6. The composition of claim 1, wherein a concentration of said active ingredient ranges between 0.01% to 50% by weight of the chaff and woody ring of the corncob.

7. The composition of claim 1, wherein a concentration of said active ingredient ranges between 0.01% to 50% by weight of the chaff ring of the corncob.

8. An absorbent composition of matter for controlled release of essential oils, comprising:
   a carrier consisting of particles and an adherent substance, wherein the particles consist of one-of a woody ring and a chaff ring of a corncob, and wherein the adherent substance is impregnated Within the carrier; and
   an active ingredient mixed with said carrier,
   wherein said active ingredient comprises an essential oil.

9. A method of manufacturing an absorbent composition of matter for controlled release of essential oils, said absorbent composition comprising a carrier consisting of particles obtained from a woody ring and a chaff ring of a corncob, said method comprising the step of mixing an active ingredient with said carrier, wherein said active ingredient comprises an essential oil.

10. The method of claim 9, wherein said essential oil is selected from the group consisting of garlic, rosemary, thyme, eugenol, mustard seed oil, or any combination thereof.

11. The method of claim 9, wherein said carrier has a content of less than 1% of fines by weight and has a moisture content below 10%.

12. The method of claim 9, wherein the particles of said carrier have a size ranging between 73 and 841 microns.

13. The method of claim 9, wherein said essential oil comprises allyl isothiocyanate (AITC).

14. The method of claim 9, wherein a concentration of said active ingredient ranges between 0.01% to 50% by weight of the chaff and woody ring of the corncob.

15. The method of claim 9, wherein a concentration of said active ingredient ranges between 0.01% to 50% by weight of the chaff ring of the corncob.

\* \* \* \* \*